United States Patent [19]

Bushell

[11] Patent Number: 4,829,074
[45] Date of Patent: May 9, 1989

[54] AZOLYL SUBSTITUTED ARALKYL COMPOUNDS AND PESTICIDAL USE THEREOF

[75] Inventor: Michael J. Bushell, Wokingham, England

[73] Assignee: Imperial Chemical Industries PLC, London, England

[21] Appl. No.: 832,424

[22] Filed: Feb. 24, 1986

[30] Foreign Application Priority Data

Mar. 6, 1985 [GB] United Kingdom ............... 8505815
Mar. 29, 1985 [GB] United Kingdom ............... 8508298

[51] Int. Cl.⁴ .................. A61K 31/49; C07D 257/04; C07D 249/04; C07D 249/08
[52] U.S. Cl. .................. 514/359; 514/381; 514/383; 514/406; 548/250; 548/252; 548/262; 548/265; 548/562
[58] Field of Search ............... 548/250, 252, 262, 265, 548/255, 562; 514/381, 383, 406, 359

[56] References Cited

U.S. PATENT DOCUMENTS

| | | | |
|---|---|---|---|
| 3,123,615 | 3/1964 | Rorig | 548/252 |
| 3,801,590 | 4/1974 | Draber et al. | 548/555 |
| 3,897,438 | 7/1975 | Draber et al. | 548/555 |
| 3,941,800 | 3/1976 | Draber et al. | 548/555 |
| 4,140,782 | 1/1979 | Timmler | 514/383 |
| 4,616,026 | 10/1986 | Richardson et al. | 548/252 |
| 4,639,527 | 1/1987 | Lantzsch et al. | 548/262 |
| 4,654,332 | 3/1987 | Parry et al. | 548/262 |

FOREIGN PATENT DOCUMENTS

| | | | |
|---|---|---|---|
| 0101288 | 2/1984 | European Pat. Off. | 548/250 |
| 86/02072 | 4/1986 | World Int. Prop. O. | 548/252 |

Primary Examiner—Glennon H. Hollrah
Assistant Examiner—D. B. Springer
Attorney, Agent, or Firm—Cushman, Darby & Cushman

[57] ABSTRACT

Compounds of the formula:

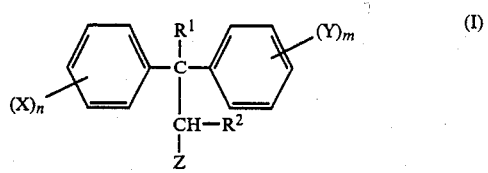

The compounds are useful as pesticides, particularly insecticides.

13 Claims, No Drawings

AZOLYL SUBSTITUTED ARALKYL COMPOUNDS AND PESTICIDAL USE THEREOF

This invention relates to novel azolyl substituted aralkyl compounds useful as pesticides in particular insecticides.

The novel compounds provided by the present invention have the general formula:

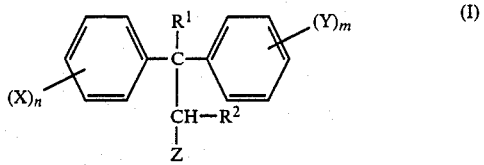

wherein $R^1$ is hydrogen or halogen, $R^2$ is methyl or ethyl, X and Y are each selected from halogen, haloalkyl, haloalkoxy, alkyl and alkoxy, m and n each have a value of zero, one or two, and Z is an azolyl group.

When n is 2, the two groups X may be the same or different. Similarly when m is 2, the two Y groups may be the same or different.

Suitable halogen groups for $R^1$ include fluorine and chlorine.

Preferably $R^1$ is hydrogen, fluorine or chlorine.

Suitably when X and/or Y is haloalkyl, alkyl and alkoxy group, they contain from 1 to 6 and preferably from 1 to 4 carbon atoms.

Preferred groups for X and Y are chloro, trifluoromethyl, trifluoromethoxy or difluoromethoxy.

Suitably m and n are both one. Preferred azolyl groups include pyrazole, triazole and tetrazole groups, in particular 1H-pyrazol-1-yl, 1,2,4-1H-triazol-1-yl, 1,2,3-1H-triazol-1-yl, 1,2,3-2H-triazol-2-yl, 1,2,3,4-2H-tetrazol-2-yl or 1,2,3,4-1H-tetrazol-1-yl.

Particular compounds of the invention include the following:

1,1-bis(4-chlorophenyl)-1-fluoro-2-(1H-pyrazol-1-yl)propane (Compound I);
1,1-bis-(4-chlorophenyl)-1-fluoro-2-(1,2,4-1H-triazol-1-yl)propane (Compound II);
1,1-bis(4-chlorophenyl)-1-fluoro-2-(1,2,3,4-2H-tetrazol-2-yl)propane (Compound III);
1,1-bis(4-chlorophenyl)-1-chloro-2-(1,2,4-1H-triazol-1-yl)propane (Compound IV);
1,1-bis(4-trifluoromethylphenyl)-1-chloro-2-(1,2,4-1H-trizol-1-yl)propane (Compound V);
1,1-bis(4-trifluoromethylphenyl)-1-fluoro-2-(1,2,4-1H-triazol-1-yl)propane (Compound VI);
1,1-bis(4-trifluoromethylphenyl)-1-fluoro-2-(1,2,3,4-2H-tetrazol-2-yl)propane (Compound VII);
1,1-bis(4-trifluoromethylphenyl)-2-(1,2,4-1H-triazol-1-yl)propane (Compound VIII);
1,1-bis(4-trifluoromethylphenyl)-2-(1,2,3,4-2H-tetrazol-2-yl)propane (Compound IX);
1,1-bis(4-trifluoromethoxyphenyl)-1-fluoro-2-(1,2,4-1H-triazol-1-yl)propane (Compound X);
1,1-bis(4-trifluoromethoxyphenyl)-1-fluoro-2-(1,2,3,4-2H-tetrazol-2-yl)propane (Compound XI);
1,1-bis(4-trifluoromethoxyphenyl)-1-fluoro-2-(1H-pyrazol-1-yl)propane (Compound XII);
1,1-bis(4-trifluoromethylphenyl)-1-fluoro-2-(1H-pyrazol-1-yl)propane (Compound XIII);
1,1-bis(4-difluoromethoxyphenyl)-1-fluoro-2-(1,2,4-1H-triazol-1-yl)propane (Compound XIV);
1,1-bis(4-difluoromethoxyphenyl)-1-fluoro-2-(1,2,3,4-2H-tetrazol-2-yl)propane (Compound XV);
1,1-bis(4-trifluoromethoxyphenyl)-2-(1,2,3,4-2H-tetrazol-2-yl)propane (Compound XVI);
1,1-bis(4-trifluoromethylphenyl)-1-chloro-2-(1,2,3,4-2H-tetrazol-2-yl)propane (Compound XVII);
1,1-bis(4-trifluoromethoxyphenyl)-1-chloro-2-(1,2,3,4-2H-tetrazol-2-yl)propane (Compound XVIII);
1,1-bis(4-methylphenyl)-1-fluoro-2-(1,2,3,4-2H-tetrazol-2-yl)propane (Compound XIX);
1,1-bis(4-fluorophenyl)-1-fluoro-2-(1,2,3,4-2H-tetrazol-2-yl)propane (Compound XX);
1,1-bis(4-prop-2-ylphenyl)-1-fluoro-2-(1,2,3,4-2H-tetrazol-2-yl)propane (Compound XXI);
1,1-bis(4-bromophenyl)-1-fluoro-2-(1,2,3,4-2H-tetrazol-2-yl)propane (Compound XXII);
1,1-bis(3-trifluoro-4-chlorophenyl)-1-fluoro(1,2,3,4-2H-tetrazol-2-yl)propane (Compound XXIII);
1,1-bis(3,4-difluorophenyl)-1-fluoro-2-(1,2,3,4-2H-tetrazol-2-yl)propane (Compound XXIV);
1-(4-chlorophenyl)-1-(4-trifluoromethylphenyl)-1-fluoro-2-(1,2,3,4-2H-tetrazol-2-yl)propane (Compound XXV);
1-(4-chlorophenyl)-1-(4-trifluoromethylphenyl)-1-chloro-2-(1,2,3,4-2H-tetrazol-2-yl)propane (Compound XXVI);
1-(4-chlorophenyl)-1-(4-trifluoromethoxyphenyl)-1-fluoro-2-(1,2,3,4-2H-tetrazol-2-yl)propane (Compound XXVII);
1-(4-ethoxyphenyl)-1-(4-trifluoromethoxyphenyl)-1-fluoro-2-(1,2,3,4-2H-tetrazol-2-yl)propane (Compound XXVIII);
1,1-bis(3-fluoro-4-trifluoromethoxyphenyl)-1-fluoro-2-(1,2,3,4-2H-tetrazol-2-yl)propane (Compound XXIX);
1-(4-trifluoromethoxyphenyl)-1-(trifluoromethylphenyl)-1-fluoro-2-(1,2,3,4-2H-tetrazol-2-yl)propane (Compound XXX);
1,1-bis(4-trifluoromethylphenyl)-1-chloro-2-(1H-pyrazol-1-yl)propane (Compound XXXI);
1,1-bis(4-trifluoromethylphenyl)-2-(1H-pyrazol-1-yl)propane (Compound XXXII);
1,1-bis(4-chlorophenyl)-2-(1,2,4-1H-triazol-1-yl)propane Compound XXXIII);
1,1-bis(4-trifluoromethoxyphenyl)-1-chloro-2-(1,2,4-1H-triazol-1-yl)propane (Compound XXXIV);
1,1-bis(4-trifluoromethoxyphenyl)-2-(1,2,4-1H-triazol-1-yl)propane (Compound XXXV);
1,1-bis(4-trifluoromethoxyphenyl)-1-fluoro-2-(1,2,3-1H-triazol-1-yl)propane (Compound XXXVI);
1,1-bis(4-trifluoromethoxyphenyl)-1-fluoro-2-(1,2,3-2H-triazol-2-yl)propane (Compound XXXVII);
1,1-bis(4-trifluoromethylphenyl)-1-fluoro-2-(1,2,3,4-1H-tetrazol-1-yl)propane (Compound XXXVIII); and
1,1-bis(4-trifluoromethoxyphenyl)-1-fluoro-2-(1,2,3,4-2H-tetrazol-2-yl)butane (Compound XXXIX).

It will be appreciated that the compounds of the invention may exist in isomeric forms due to the presence of one or two chiral centres and the invention includes each of the isomeric forms in isolation as well as mixtures, including racemic mixtures of the said isomeric forms.

Further according to the invention, there is provided a process for preparing a compound of formula (I) which process comprises halogenation of a compound of formula (II):

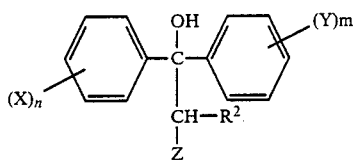 (II)

wherein X, Y, Z, m and n are as defined in relation to formula (I), and thereafter if desired converting the halogen atom introduced to a hydrogen atom.

The halogenation is carried out using conventional halogenating agents such as thionyl chloride or diethylaminosulphurtrifluoride under conventional conditions. For example, chlorination is suitably carried out in an inert organic solvent such as acetonitrile at moderate temperature for example of from 0° C. to 60° C., conveniently at ambient temperature. The reaction may be carried out in the presence of a base such as imidazole.

Fluorination is suitably carried out in an inert organic solvent such as dichloromethane at low temperatures of for example from −78° C. to 20° C.

Reduction of the compound of formula (I) wherein $R^1$ is halogen to a compound of formula (I) where $R^1$ is hydrogen can be effected by a conventional reducing agent such as tributyltin hydride. In this case the reduction is suitably effected in an inert organic solvent such as toluene, optionally in the presence of a catalyst such as α,α′azoisobutyronitrile (AIBN).

Alternatively compounds of formula (I) wherein $R^1$ is hydrogen can be prepared by hydrogenation of a compound of formula (III):

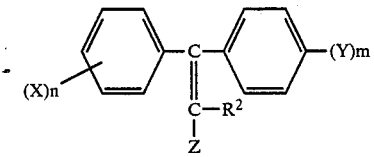 (III)

wherein $R^2$, X, Y, Z, m and n are as defined in relation to formula (I).

Hydrogenation is suitably effected by conventional methods, for example using hydrogen in the presence of a catalyst such as palladium under elevated pressures of up to 110 atmospheres.

Compounds of formula (III) can be prepared by dehydration of a compound of formula (II). Again conventional methods can be employed to effect the dehydration, one example being to react the compound of formula (II) with a dehydrating agent such as toluene sulphonic acid in an inert organic solvent for example benzene or toluene.

Elevated temperatures, conveniently the reflux temperature of the solvent, are suitably employed.

Some compounds of formula (II) are described and claimed in our copending UK patent application No. 2156807A and European patent application No. 85306474. Certain compounds of formula (II) are novel, and as such form part of the invention. They may have insecticidal properties in their own right.

Therefore further according to the invention there is provided a compound of formula (IIA):

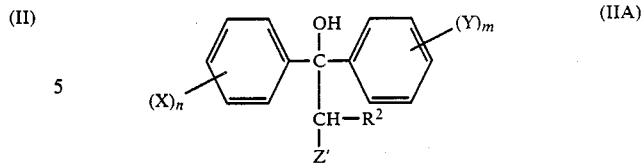 (IIA)

wherein $R^2$, X, Y, m and n are defined in relation to formula (I) and Z′ is Z as defined in relation to formula (I) with the proviso that when Z′ is 1,2,3,4-2H-tetrazole, $R^2$ is ethyl or n and m are other than one except that the compound may be 1-(4-trifluoromethylphenyl)-1-(4-trifluoromethoxyphenyl)-2-(1,2,3,4-2H-tetrazol-2-yl)propan-1-ol; and with the further proviso that when Z′ is an azolyl group containing 2 or 3 nitrogen atoms other than 1,2,3-1H-triazol-1-yl or 1,2,3-2H-triazol-2-yl, $R^2$ is ethyl.

Suitable compounds of formula IIA are set out in Table I below.

TABLE I

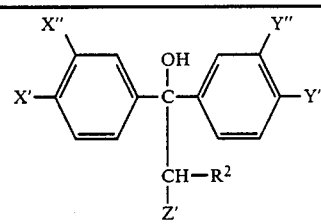

| Compound No. | X′ | X″ | Y′ | Y″ | Z′ | $R^2$ |
|---|---|---|---|---|---|---|
| XXXX | $OCF_3$ | H | $OCF_3$ | H | 1,2,3-1H—triazole | $CH_3$ |
| XXXXI | $OCF_3$ | H | $OCF_3$ | H | 1,2,3-2H—triazole | $CH_3$ |
| XXXXII | $CF_3$ | H | $CF_3$ | H | 1,2,3-1H—triazole | $CH_3$ |
| XXXXIII | $CF_3$ | H | $CF_3$ | H | 1,2,3-2H—triazole | $CH_3$ |
| XXXXIV | $CF_3$ | H | $CF_3$ | H | 1,2,3,4-1H—tetrazole | $CH_3$ |
| XXXXV | $OCF_3$ | H | $OCF_3$ | H | 1,2,3,4-2H—tetrazole | $CH_2CH_3$ |
| XXXXVI | $CF_3$ | H | $OCF_3$ | H | 1,2,3,4-2H—tetrazole | $CH_3$ |
| XXXXVII | $OCF_3$ | F | $OCF_3$ | F | 1,2,3,4-2H—tetrazole | $CH_3$ |

Compounds of formulae (II) or (IIA) where (X)n is the same as (Y)m can be prepared by reaction of a compound of formula (IV):

$$Z-\overset{R^2}{\underset{|}{CH}}-CO_2R^3 \quad \text{(IV)}$$

wherein Z is as defined in relation to formula (I) and/or $R^3$ is an alkyl group, for example a $C_{1-6}$ alkyl such as methyl; with a Grignard reagent of formula (V):

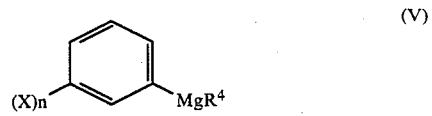 (V)

wherein X and n are as defined in relation to formula (I) and $R^4$ is halogen such as bromine.

The reaction conditions are suitably those conveniently employed in a Grignard type reaction ie. using an inert organic solvent such as tetrahydrofuran or diethyl ether at a temperature of from −20° C. up to the boiling point of the solvent and, preferably at room temperature or under reflux.

Compounds of formula (IV) can be prepared by reacting an azole with a compound of formula (VI):

(VI)

where $R^2$ is as defined in relation to formula (I), $R^3$ is as defined in relation to formula (IV) and $R^5$ is a leaving group such as halogen.

A preferred leaving group $R^5$ is bromine. The reaction is suitably effected in an inert organic solvent such as acetonitrile or acetone in the presence of a base such as potassium carbonate. Preferably the reaction is carried out under reflux.

Compounds of formula (V) and (VI) are either known compounds or they can be prepared from known compounds by conventional methods.

Compounds of formula (II) or (IIA) may also be prepared by reacting a compound of formula (VII):

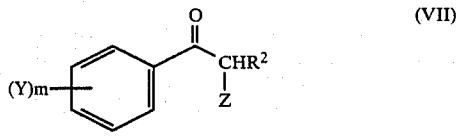
(VII)

wherein $R^2$, Y, Z and m are as defined in relation to formula (I), with a compound of formula (V) as hereinbefore defined. Conventional Grignard reaction conditions as outlined hereinbefore are suitably employed.

Compounds of formula (VII) can be prepared by reacting a compound of formula (VIII):

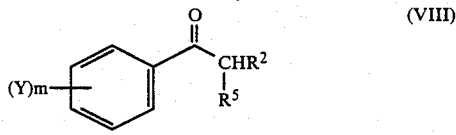
(VIII)

wherein $R^2$, Y and m are as defined in relation to formula (I) and $R^5$ is a leaving group, with an azole.

Suitable leaving groups $R^5$ include halogen such as bromine or chlorine. The reaction is suitably carried out in an inert organic solvent such as acetone, in the presence of a base such as potassium carbonate. Preferably the reaction is carried out under reflux conditions.

Compounds of formula (VIII) can be prepared by appropriate derivitisation of a compound of formula (IX):

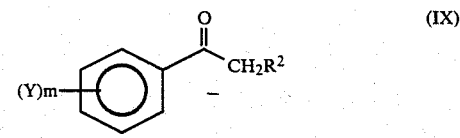
(IX)

wherein $R^2$, Y and m are as defined in relation to formula (I).

For example, when $R^5$ is bromine, the compound of formula (IX) can be reacted with bromine in an organic solvent such as carbon tetrachloride.

Compounds of formula (IX) are either known compounds or they can be prepared from known compounds by known methods.

One sequence for the preparation of a compound of formula (I) is illustrated with respect to the preparation of 1,1-bis(4-trifluoromethoxyphenyl)-1-fluoro-2-(1,2,3,4-2H-tetrazol-2-yl)propane as follows:

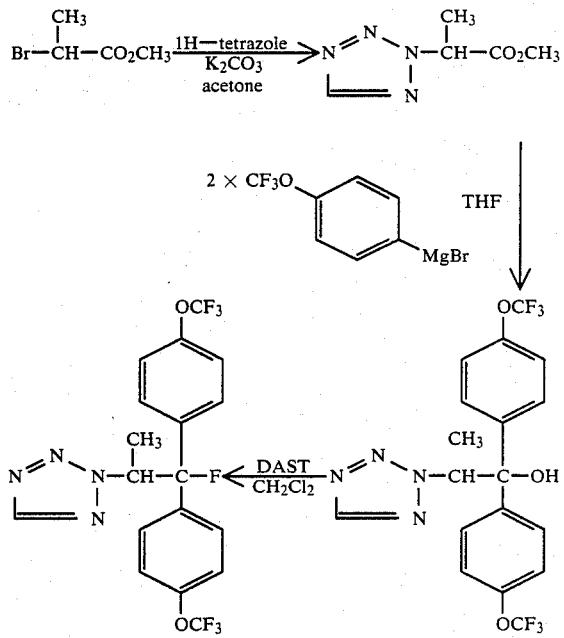

(DAST is diethylaminosulphurtrifluoride).

The details of these procedures are set out in the Examples hereinafter.

The compounds of formulae (I) or (IIA) may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient of ingredients of formulae (I) or (IIA) suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnapthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alochol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparation which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The rate of application of the compounds of the invention will depend upon a number of factors such as the type of pest involved and the degree of infestation etc. However, in general a rate of from 0.01 to 10 kg/ha of active ingredient will be applied.

The compositions of the invention are toxic to a variety of insect and other invertebrate pests, including, for example, the following:
*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
*Aonidiella* spp. (scale insects)
*Trialeuroides* spp. (white flies)
*Blattella germanica* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
*Chilo partellus* (maize stem borers)
*Anthonomus grandis* (boll weevils)
*Leptinotarsa decimlineata* (colorado potato beetle)

The compounds of formula I and compositions comprising them have shown themselves to be particularly useful in controlling lepidopteran pests of cotton, for example Spodoptera spp. and Heliothis spp. The compounds may also be used to combat pests which inhabitat the soil, for example Diabrotica spp. They may also be useful in combating insect and acarine pests which infest domestic animals, such as *Lucilia sericata*, and ixodid ticks such as Boophilus spp., Ixodes spp., Amblyomma spp., Rhipicephalus spp., and Dermaceutor spp. They may be effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterized by means of nuclear magnetic resonance spectroscopy and infra red spectroscopy. In each case where a product is specifically named its spectral characteristics are consistent with the assigned structure.

EXAMPLE 1

This Example illustrates the preparation of methyl 2-(1,2,3,4-1H-tetrazol-1-yl)propionate and 2-(1,2,3,4-2H-tetrazol-2-yl)propionate.

A mixture of methyl 2-bromopropionate (66.8 g), 1H-tetrazole (28.02 g), anhydrous potassium carbonate (110 g) and acetone (1000 cm$^3$) was stirred together at the ambient temperature (ca. 18° C.) for 1 hour and then at reflux temperature for four hours. After keeping the mixture for a further 16 hours at the ambient temperature the insoluble component was removed by filtration and the filtrate concentrated by evaporation of the solvent under reduced pressure. The residual oil (60 g) was subjected to distillation and the fraction having a boiling point range from 78°–93° C. at 0.35 to 2.5 mm Hg collected to yeild methyl 2-(1,2,3,4-2H-tetrazol-2-yl)propionate (A; 22.3 g). The undistillable residue was dissolved in dichloromethane and purified by elution through a short silica column. The collected eluate was concentrated by evaporation of the solvent under reduced pressure to yield methyl 2-(1,2,3,4-1H-tetrazol-1-yl)propionate (B; 35 g, 99% pure by gas/liquid chromatographic analysis).

NMR (CDCl$_3$) δ: (A) 1.98 (d, 3H); 3.77 (s, 3H); 5.70 (q, 1H); 8.58 (s, 1H); (B) 1.95 (d, 3H); 3.81 (d, 3H); 5.58 (q, 1H); 8.95 (s, 1H).

Infra red (liquid film): (A) 1758 cm$^{-1}$

EXAMPLE 2

By use of procedures similar to those described in Example 1, the following esters were prepared:

(i) Ethyl-2-(2H-tetrazol-2-yl)propionate (oil)

NMR CDCl$_3$, δ: 1.24 (3H, t); 2.0 (3H, d); 4.2 (2H, q); 5.73 (1H, q); 8.59 (1H, s), and its isomer as a solid.

Ethyl-2-(1H-tetrazol-1-yl)propionate

NMR CDCl$_3$ δ: 1.29 (3H, t); 1.94 (3H, d); 4.26 (2H, q) 5.60 (1H, q); 8.97 (1H, s).

(ii) Methyl-2-(2H-tetrazol-2-yl)butyrate (isolated by distillation)

NMR CDCl$_3$ δ: 0.94 (t, 3H); 2.48 (m, 2H); 3.78 (s, 3H); 5.74 (m, 1H); 8.62 (s, 1H).

The distillation residue in this experiment was about 90% pure and was identified as methyl-2-(1H-tetrazol-1-yl)butyrate.

NMR CDCl$_3$ δ: 0.95 (3H, t); 2.3 (2H, m); 3.82 (3H, s); 5.45 (1H, dd); 9.0 (1H, s).

EXAMPLE 3

This Example illustrates the preparation of 1,1-bis(4-trifluoromethoxyphenyl)-2-(1,2,3,4-2H-tetrazol-2-yl)propan-1-ol.

A solution of 4-trifluoromethoxybromobenzene (45.79 g) in dry tetrahydrofuran (200 cm$^3$) was added carefully to a stirred mixture of magnesium turnings (4.56 g), iodine (1 crystal) and dry tetrahydrofuran (70 cm$^3$). The reaction commenced after about 20 cm$^3$ of the solution had been added, and the reaction was maintained at the reflux temperature whilst the remainder of the solution was added, and thereafter for a further 1 hour. The mixture was cooled to the ambient temperature and a solution of methyl 2-(1,2,3,4-2H-tetrazol-2-yl)propionate (13.95 g), in dry tetrahydrofuran (60 ml) added dropwise, after which the mixture was heated at the reflux temperature for 30 minutes. The mixture was cooled and poured into water (500 cm$^3$) and acidified with 2N hydrochloric acid (250 cm$^3$). The aqueous mixture was extracted with diethylether (3×400 cm$^3$), the ethereal extracts combined, dried over anhydrous magnesium sulphate, and concentrated by removal of the solvent by evaporation under reduced pressure. The residual oil (30.5 g) was subjected to purification by chromatography using a silica gel column eluted with a mixture of hexane (4 parts by volume) and ethylacetate (1 part by volume), and by hplc to yield 1,1-bis(4-trifluoromethoxyphenyl)-2-(1,2,3,4-2H-tetrazol-2-yl)propan-1-ol as a colourless oil (10 g) which crystallized on standing (mp. 55°-58° C.).

NMR (CDCl$_3$) δ: 1.54 (d, 3H); 4.82 (s, 1H); 6.13 (q, 1H); 6.9-7.7 (m, 8H); 8.38 (s, 1H).

EXAMPLE 4

By the use of procedures similar to those illustrated in Examples 1 to 3, and with the appropriate analogous starting materials, the following azolyl substituted propanols were also prepared.

(i) 1,1-bis(4-chlorophenyl)-2-(1,2,3,4-2H-tetrazol-2-yl)propan-1-ol;

$^1$H NMR (CDCl$_3$): δ 1.53 (d, 3H); 4.76 (s, 1H); 6.1 (q, 1H); 7.0-7.6 (m, 8H); 8.38 (s, 1H).

(ii) 1,1-bis(4-trifluoromethylphenyl)-2-(1,2,3,4-H-tetrazol-2-yl)propan-1-ol;

$^1$H NMR CDCl$_3$ δ: 1.55 (d, 3H); 4.95 (s, 1H); 6.23 (q, 1H); 7.68 (m, 8H); 8.4 (s, 1H).

IR 3500 cm$^{-1}$ OH.

(iii) 1,1-bis (3,4-difluorophenyl-2-(1,2,3,4-2H-tetrazol-2-yl)propan-1-ol;

$^1$H NMR CDCl$_3$ δ: 1.55 (d, 3H); 4.85 (s, 1H); 6.07 (q, 1H); 6.8-7.6 (m, 6H); 8.4 (s, 1H).

$^{19}$F NMR 2 signals (multiplets) at −136 and −139 ppm (relative to CFCl$_3$).

(iv) 1,1-bis(3-trifluoromethyl-4-chlorophehyl)-2-(1,2,3,4-2H-tetrazol-2-yl)propan-1-ol;

$^1$H NMR CDCl$_3$δ: 1.55 (3H, d); 5.0 (s, 1H); 6.15 (q, 1H); 7.2-8.0 (m, 6H); 8.44 (s, 1H).

(v) 1,1-bis(4-prop-2-ylphenyl)-2-(1,2,3,4-2H-tetrazol-2-yl)propan-1-ol; (purified by chromatography and then recrystallized).

$^1$H NMR CDCl$_3$δ: 1.12 and 1.24 (each 6H, d); 1.53 (d, 3H); 2.8 (m, 2H); 4.54 (s, 1H); 6.13 (q, 1H); 6.9-7.6 (m, 8H); 8.37 (s, 1H).

(vi) 1,1-bis(4-fluorophenyl)-2-(1,2,3,4-2H-tetrazol-2-yl)propan-1-ol;

$^1$H NMR CDCl$_3$δ: 1.53 (d, 3H); 4.71 (s, 1H); 6.14 (q, 1H); 6.7-7.6 (m, 8H); 8.38 (s, 1H).

(vii) 1,1-bis(4-methoxyphenyl)-2-(1,2,3,4-2H-tetrazol-2-yl)propan-1-ol); (purified by column chromatography and crystallised by trituration with hexane); mp. 131°-134° C.;

$^1$H NMR CDCl$_3$δ: 1.53 (d, 3H); 3.65 and 3.76 (each s, 3H); 4.50 (s, 1H), 6.10 (q, 1H); 6.6-7.6 (8H, m); 8.36 (s, 1H).

(viii) 1,1-bis(4-methylphenyl)-2-(1,2,3,4-2H-tetrazol-2-yl)propan-1-ol;

$^1$H NMR CDCl$_3$δ: 1.54 (d, 3H); 2.17 and 2.30 (each 3H, s); 4.55 (s, 1H); 6.16 (q, 1H); 6.7-7.5 (m, 8H); 8.35 (s, 1H).

In a similar manner, the following azolyl substituted propanols may also be prepared.

(ix) 1,1-bis(4-trifluoromethoxyphenol)-2-(1H-pyrazol-1-yl)-propan-1-ol).

(x) 1,1-bis(4-trifluoromethylphenyl)-2-(1,2,4-1H-triazol-1-yl)propan-1-ol.

(xi) 1,1-bis(4-chlorophenyl)-2-(1H-1,2,4-1-yl)propan-1-ol.

(xii) 1,1-bis(4-trifluoromethoxyphenyl)-2-(1H-1,2,4-triazol-1-yl)propan-1-ol.

EXAMPLE 5

This Example illustrates the preparation of 1,1-bis(4-trifluoromethylphenyl)-2-(1,2,3,4-1H-tetrazol-1-yl)propan-1-ol.

The Grignard reagent formed from 4-trifluoromethylbromobenzene (by a method as outlined in Example 3) was reacted with methyl 2-(1,2,3,4-1H-tetrazol-1-yl)propionate (Example 1B) to give the title compound. Purification was by chromatography on silica gel, the desired product being eluted with ethyl acetate. The material was obtained as an oil.

$^1$H NMR, CDCl$_3$ δ: 1.58 (3H, d); 4.64 (1H, s); 5.88 (1H, q); 7.48 and 7.68 (each 4H, s); 8.70 (1H, s).

$^{19}$F NMR (relative to CFCl$_3$) −63.26, −63.36 (each a singlet).

EXAMPLE 6

This Example illustrates the preparation of the following propanols.

[Structure diagram: diphenyl compound with X and Y substituents on para positions, central carbon bearing OH and tetrazolyl group (N=N-N-N=)]

| | X | Y |
|---|---|---|
| (1) | Br | Br |
| (2) | Br | H |
| (3) | H | H |

The procedures were carried out in a similar manner to that described in Example 3 using 1,4-dibromobenzene instead of 4-trifluoromethoxybromo benzene.

The crude product was a very complex mixture. An initial separation on silica gel eluting with hexane/ethylacetate (4:1) gave a fraction containing largely three components in a ratio 58:33:9 containing two, one and no bromine atoms. These three components were separated using reverse phase h.p.l.c. The dribromoanalogue (1 above) was obtained pure (eluting with 3:2 acetonitrile/water mixture on a Waters C-18 support).

$^1$H NMR CDCl$_3$ δ: 1.55 (d, 3H); 4.75 (s, 1H); 6.13 (q, 1H); 7.3–7.5 (m, 8H); 8.40 (s, 1H).

EXAMPLE 7

This Example illustrates the preparation of 1,1-bis(4-hydroxyphenyl)-2-(1,2,3,4-2H-tetrazol-2-yl)propan-1-ol.

Step A

4-Bromophenol (32.87 g) and t-butyldimethylsilylchloride (31.5 g) in dry dimethylformamide (150 ml) were stirred under nitrogen. Imidazole (28.46 g) was added and the mixture stirred for 6 hours. The reaction was poured into 5% aqueous sodium bicarbonate solution (750 ml) and extracted with diethyl ether (3×400 ml). The ether layers were combined, washed with water (3×200 ml), dried over MgSO$_4$ and evaporated to a yellow oil 56.3 g. This was purified by passing through a silica column eluting with hexane/ethylacetate (3:1) to give a pale yellow coloured oil (55 g), 97% pure by glc.

Step B

The reaction was carried out as described in Example 5 except that the Grinard reaction was initiated by using an ultrasonic bath, 5.75 g of the O-(t-butyldimethylsilyl)-4-bromophenol from step A was used as starting material, and that for the work up the mixture was poured into iced saturated aqueous ammonium chloride (250 ml) and the product extracted into diethyl ether (ie. avoiding strongly acidic conditions).

The product was purified by h.p.l.c. on silica gel eluting with hexane/ethyl acetate (4:1) to give a solid (0.55 g, 11%).

$^1$H NMR CDCl$_3$ δ: ca 0.1, 0.2 (2 singlets, 12H); ca 0.9 (2 singlets 18H); 1.55 (d, 3H); 4.53 (s, 1H); 6.1 (q, 1H); 6.6–7.5 (m, 8H); 8.4 (s, 1H).

IR 3510 cm$^{-1}$ OH other peaks at 1615, 1510, 1270, 1180, 925, 845 cm$^{-1}$.

Step C

The bis(t-butyldimethylsilyl)protected phenol from step (b) (1.08 g) was mixed with acetic acid/water/methanol (80 ml 2:1:1). The mixture was heated at 95° C. for 6½ hours. Ethyl acetate was added to the cooled mixture and the organic layer washed with water (50 ml) saturated sodium bicaronate solution (3×), water (2×30 ml) then dried over MgSO$_4$ and evaporated to a brown solid (0.76 g). This was dissolved in ethyl acetate/hexane and the title compound precipitated out as a white solid (0.35 g), mp. 209°–212° C.

$^1$H NMR d$^4$-methanol δ: 1.6 (d, 3H); 6.2 (q, 1H); 6.5-7.6 (m, 8H); 8.53 (s, 1H).

EXAMPLE 8

This Example illustrates the preparation of 1,1-bis(4-difluoromethoxyphenyl)-2-(1,2,3,4-2H-tetrazol-2-yl)propan-1-ol.

The bisphenol (0.25 g) from Example 7 in tetrahydrofuran (3 ml) with aqueous sodium hydroxide (0.32 g, NaOH in in 2.5 ml H$_2$O) was warmed at 65° C. with stirring. Bromodifluoromethane gas was bubbled through the solution with vigorous stirring for 3 hours. The mixture was then poured into water (30 ml) and extracted with ether (3×20 ml). The ether layers were dried over MgSO$_4$ and evaporated to a brown oil. This was purified by preparative h.p.l.c. on silica gel eluting with ethylacetate/hexane (2:3) to give the desired bis(-difluoromethoxyphenyl)tetrazole (29 mg).

$^1$H NMR CDCl$_3$ δ: 1.55 (3H, d); 4.73 (s, 1H); 6.15 (q, 1H); 6.4 and 6.5 (each t, 1H with large coupling constant to fluorine 80 Hz); 6.9–7.6 (m, 8H; 8.4 (s, 1H).

This compound can be converted to the corresponding fluoropropane by fluorination as described in Example 14.

EXAMPLE 9

This Example illustrates the preparation of isomeric α-(1H and 2-H-tetrazolyl)-4-chloropropiophenones.

Tetrazole (5 g), α-bromo-4-chloropropiophenone (15 g) and potassium carbonate (10 g) were heated at 60° C. in acetonitrile for 40 minutes. The mixture was poured into water and extracted into ethylacetate. The organic layer was washed with water, dried and evaporated to a solid (14 g). 7 g of this material was purified on a silica gel column, eluting with 30% ethyl acetate/hexane to collect a fast running compound, and 5% MeOH/CHCl$_3$ to collect the more polar isomer. These were crystallised from CHCl$_3$/hexane.

Fast-running isomer 2.5 g identified as α-(1,2,3,4-2H-tetrazol-2-yl)4-chloropropiophenone.

$^1$H NMR δ 2.0 (d, 3H); 6.9 (q, 1H); 7.5–8.1 (m, 4H); 8.78 (s, 1H).

Polar isomer 2.35 g identified as α-(1,2,3,4-1H-tetrazol-1-yl)-4-chloropropiophenone.

$^1$H NMR δ 1.97 (d, 3H); 6.8 (q, 1H); 7.5–8.2 (m, 4H); 9.45 (s, 1H).

EXAMPLE 10

This Example illustrates the preparation of α-(tetrazolyl)-4-ethoxypropiophenone. The procedures employed were analogous to that described in Example 9 except that acetone was used as the solvent. The separation of the isomers was effected using column chromatography.

A. α-(1,2,3,4-2H-tetrazol-2-yl)4-ethoxypropiophenone 1.44 (3H, t); 2.03 (d, 3H); 4.11 (q, 2H); 6.55 (q, 1H); 6.95 and 7.92 (each 2H, m); 8.55 (s, 1H), mp. 56°–58° C.

B. Polar isomer α-(1,2,3,4-1H-1-tetrazol-1-yl)4-ethoxypropiophenone 1.45 (3H, t); 1.9 (d, 3H); 4.13 (q, 2H); 6.56 (q, 1H), 7.0 and 8.0 (each 2H, m); 8.96 (s, 1H). mp. 85°–87° C.

EXAMPLE 11

This Example illustrates the preparation of 1-(4-chlorophenyl)-1-(4-trifluoromethylphenyl)-2-(1,2,3,4-2H-tetrazol-2-yl)propan-1-ol.

4-trifluoromethylphenylmagnesium bromide was prepared in a manner analogous to that described in Example 3 from magnesium (0.2 g) in THF (6 ml) and 4-bromotrifluoromethylbenzzene (1.8 g).

The α-(2-tetrazol-2-yl)4-chloropropiophenone (1.9 g) from Example 11 in tetrahydrofuran (6 ml) was added dropwise. The mixture was stirred for 1 hour and then poured into water (30 ml), with 3M aqueous hydrochloric acid (30 ml) being added. The mixture was extracted with diethyl ether (3×40 ml), the combined extracts being dried over MgSO$_4$ and evaporated to a brown oil 3.3 g. After purification by h.p.l.c. on silica gel eluting with hexane/ethyl acetate (4:1) a colourless oil was produced (2.8 g) which crystallised to give the title compound m.pt 123°–125° C.

$^1$H NMR CDCl$_3$ δ: 1.55 (d, 3H); 4.85 (s, 1H); 6.18 (q, 1H); 7.2–7.7 (m, 8H); 8.38 (s, 1H).

EXAMPLE 12

Using procedures similar to that described in Example 11, the following compounds were prepared:

(i) 1-(4-chlorophenyl)-1-(4-trifluoromethoxyphenyl)-2-(1,2,3,4-2H-tetrazol-2-yl)propan-1-ol;

$^1$H NMR CDCl$_3$ δ: 1.55 (d, 3H); 4.8 (s, 1H); 6.12 (q, 1H); 7.0 (m, 2H and 7.3–7.6 (m, 6H); 8.38 (s, 1H).

(ii) 1-(4-ethoxyphenyl)-1-(4-trifluoromethoxyphenyl)-2-(1,2,3,4-2H-tetrazol-2-yl)propan-1-ol;

$^1$H NMR CDCl$_3$ δ: 1.3 (t, 3H); 1.55 (d, 3H); 4.03 (q, 2H); 4.7 (s, 1H); 6.13 (q, 1H); 6.8–7.6 (m, 8H); 8.38 (s, 1H).

EXAMPLE 13

This Example illustrates the preparation of 1,1-bis(trifluoromethoxyphenyl)-2-(1,2,3,4-2H-tetrazol-2-yl)butan-1-ol.

The Grignard reagent from 4-bromotrifluoromethoxybenzene was prepared as previously described in Example 3 and reacted with methyl-2-(2-H-tetrazol-2-yl)butyrate from Example 2ii, in a similar manner to that described in Example 3.

The title product was purified by h.p.l.c.

$^1$H NMR CDCl$_3$ δ: 0.87 (t, 3H); 1.5–2.4 (complex m, 2H); 4.78 (s, 1H); 5.9 (dd, 1H); 7–7.7 (m, 8H); 8.41 (s, 1H).

EXAMPLE 14

This Example illustrates the preparation of 1,1-bis(4-trifluoromethoxyphenyl)-1-fluoro-2-(1,2,3,4-2H-tetrazol-2-yl)propane (Compound XI).

A solution of 1,1-bis(4-trifluoromethoxyphenyl)-2-(1,2,3,4-2H-tetrazol-2-yl)propan-1-ol (3.5 g) prepared as described in Example 3 in dichloromethane (50 cm$^3$) was added dropwise to a stirred solution of diethylaminosulphurtrifluoride (1.51 g) kept at a temperature of −70° C. under a nitrogen atmosphere. After 1 hour a further quantity of diethylaminosulphurtrifluoride (1.5 g) was added and the mixture stirred for 18 hours at the ambient temperture, during which time any vapours emitted were vented through a column of potassium hydroxide pellets. Water (30 cm$^3$) was added carefully to the mixture, the organic layer separated and washed with more water (3×30 cm$^3$), dried over anhydrous magnesium sulphate and concentrated by evaporation of the solvent under reduced pressure. The residual oil (4.5 g) was purified by hplc using a silica gel column eluted with a mixture of hexane (5 parts by volume and ethylacetate (1 part by volume) to yield 1,1-bis(4-trifluoromethoxyphenyl)-1-fluoro-2-(1,2,3,4-2H-tetrazol-2-yl)propane as an oil (3.19 g) which crystallised on standing (mp. 68°–70° C.).

NMR (CDCl$_3$) δ: 1.76 (d, 3H); 5.86, 6.2 (2q, 1H*); 6.9–7.77 (m, 8h); 8.35 (s, 1H).
(* split by CH$_3$ and F, J=7 and 27 Hz)

EXAMPLE 15

By a procedure similar to that exemplified in Example 14 the following azolyl-substituted fluoropropanes were obtained from the corresponding azolyl-substituted propanols.

(i) 1,1-bis(4-trifluoromethoxyphenyl)-1-fluoro-2-(1H-pyrazol-1-yl)propane (Compound XII).

$^1$H NMR (CDCl$_3$) δ: 1.54 (d, 3H); 5.3, 5.6 (dq, 1H*); 6.1 (t, 1H); 6.9–7.6 (m, 10H).
(* split by CH$_3$ and F, J=7 and 32 Hz).

(ii) 1,1-bis(4-chlorophenyl)-1-fluoro-2-(1,2,3,4-2H-tetrazol-2-yl)propane (Compound III) (mp. 77°–79° C).

$^1$H NMR (CDCl$_3$) δ: 1.72 (d, 3H); ca. 6.0 (dq, 1H); 7.15 (s, 4H); 7.45 (s, 4H); 8.36 (s, 1H).

(iii) 1,1-bis(4-trifluoromethylphenyl)-1-fluoro-2-(1,2,4-1H-triazol-1-yl)propane (Compound VI)

$^1$H NMR CDCl$_3$ δ ppm: 1.58 (3H, d); ca 5.6 (1H, dq); 7.5 and 7.7 (each 4.H, s); 7.75 and 8.2 (each 1H broadened singlets).

(iv) 1,1-bis(4-trifluoromethylphenyl)-1-fluoro-2-(1,2,3,4-2H-tetrazol-2-yl)propane (Compound VII)

melting point 102°–104° C.

$^1$H NMR CDCl$_3$ δ ppm: 1.78 (3H, d); 6.06 (1H, dq); ca. 7.45 and 7.75 (each 4H, m); 8.37 (1H, s).

(v) 1,1-bis(4-methylphenyl)-1-fluoro-2-(2H-tetrazol-2-yl)propane (Compound XIX)

melting point 115°–117° C. (yellowish crystals).

$^1$H NMR CDCl$_3$ δ ppm: 1.73 (3H, d); 2.20 and 2.36 (each 3H, s); ca 6.02 (1H, dq); 6.9–7.5 (8H, m); 8.34 (1H, s).

(vi) 1,1-bis(4-fluorophenyl)-1-fluoro-2-(2H-tetrazol-2-yl)propane (Compound XX).

White solid m.pt 76°–79° C.

$^1$H NMR CDCl$_3$ δ ppm: 1.75 (3H, d); ca. 6.0 (1H, dq); 6.7–7.6 (8H, m); 8.36 (1H, s).

(vii) 1,1-bis(4-prop-2-ylphenyl)-1-fluoro-2-(2H-tetrazol-2-yl)propane (Compound XXI).

Melting point 99°–101° C.

$^1$H NMR CDCl$_3$ δ ppm: 1.13 and 1.25 (each 6H, d); 1.7 (3H, d); 2.5–3.1 (2H, m); ca 6.0 (1H, dq); 6.9–7.5 (8H, m); 8.32 (1H, s).

(viii) 1,1-bis(4-bromophenyl)-1-fluoro-2-(2H-tetrazol-2-yl)propane. (Compound XXII).

Melting point 95°–98° C.

$^1$H NMR CDCl$_3$ δ ppm: 1.74 (3H, d); ca. 6.0 (1H, dq); 7.0–7.7 (8H, m); 8.36 (1H, s).

(ix) 1,1-bis(3-trifluoromethyl-4-chlorophenyl)-1-fluoro-2-(2H-tetrazol-2-yl)propane (Compound XXIII).

Melting point 128°–130° C.

$^1$H NMR CDCl$_3$ δ ppm: 1.77 (3H, d); ca. 6.05 (1H, dq); 7.35–7.9 (6H; m); 8.4 (1H, s).

$^{19}$Fnmr δ (ppm) relative to CFCl$_3$: −63.34, −63.44 (each 3F); −166.5 (1H, d JHF 25 Hz).

(x) 1,1-bis(3,4-difluorophenyl)-1-fluoro-2-(2H-tetrazol-2-yl)propane (Compound XXIV).

Prepared as a colourless oil.

$^1$H NMR CDCl$_3$ δ ppm: 1.75 (3H, d); ca. 6.0 (1H, dq); 6.9–7.5 (6H, m); 8.38 (1H, s).

(xi) 1-(4-chlorophenyl)-1-(4-trifluoromethylphenyl)-1-fluoro-2-(2H-tetrazol-2-yl)propane (Compound XXV).

(colourless oil)

$^1$H NMR CDCl$_3$ δ ppm: ca. 1.75 (3H, 2 overlapping doublets)*, ca. 6.0 (1H, dq); 7.2–7.7 (8H, m); 8.36, 8.38 (total 1H, as 2 singlets)*

$^{19}$F NMR CDCl$_3$ δ ppm: relative to CFCl$_3$: ca. −63.4* (3F as 2 singlets); ca. −168* (1F as 2 doublets).

*These signals indicate that this compound is a mixture of diastereoisomers in approximately equal ratio.

(xii) 1-(4-chlorophenyl)-1-(4-trifluoromethoxyphenyl)-1-fluoro-2-(2H-tetrazol-2-yl)propane (Compound XXVII).

$^1$H NMR CDCl$_3$ δ ppm: ca. 1.77* (total 3H, 2 overlapping doublets) ca. 6.05 (1H, dq); 7.0–7.6 (8H, m); 8.35, 8.36* (total 1H 2 singlets).

These signals show the presence of 2 diastereoisomers in approximately equal amounts.

(xiii) 1-(4-ethoxyphenyl)-1-(4-trifluoromethoxyphenyl)-1-fluoro-2-(2H-tetrazol-2-yl)propane (Compound XXVIII).

$^1$H NMR CDCl$_3$ δ ppm: ca. 1.4* (total 3H, 2 overlapping triplets); ca. 1.75* (3H, 2 overlapping doublets); ca. 6.0 (1H, dq); 6.6–7.6 (8H, m); 8.35, 8.37 (total 1H, 2 singlets).

*The signals show the presence of 2 diastereoisomers in approximately 60/40 ratio.

(xiv) 1,1-bis(4-trifluoromethoxyphenyl)-1-fluoro-2-(2H-tetrazol-2-yl)butane (Compound XXXIX).

$^1$H NMR CDCl$_3$ δ ppm: 0.7 (3H, t); 1.7–2.8 (2H complex multiplet); ca. 5.7 (1H as 4 doublets J 2.6, 11.5 and 26.2 Hz); 6.9–7.7 (8H, m); 8.37 (H, s).

(xv) 1,1-bis(4-chlorophenyl)-1-fluoro-2-(1H-1,2,4-triazol-1-yl)propane (Compound II).

Prepared as a gum.

$^1$H NMR CDCl$_3$ δ ppm: 1.57 (3H, d); ca. 5.5 (1H, dq); 7.2 and 7.4 (each 4H, s); 7.75 (1H, s) and 8.14 (1H, d, J 2 Hz, long range coupling to F).

(xvi) 1,1-bis(4-trifluoromethoxyphenyl)-1-fluoro-2-(1H-1,2,4-triazol-1-yl)propane (Compound X).

Prepared as a gum.

$^1$H NMR CDCl$_3$ δ ppm: 1.6 (3H, d); ca. 5.5 (1H, dq); 7.0–7.6 (8H, m); 7.75 (1H, s); 8.16 (1H, d, J2-3 Hz-long range coupling to the F).

EXAMPLE 16

α-(2H-tetrazol-2-yl)p-trifluoromethylpropiophenone was prepared by analogous methods to those described in Example 10, being separated from its 1H-isomer by chromatography on silica gel to give pure product.

$^1$H NMR CDCl$_3$ δ ppm: 2.02 (3H, d); 6.58 (1H, q); 7.75 and 8.02 (each 2H ABq); 8.56 (1H, s).

$^{13}$C nmr CDCl$_3$ (ppm) 191.37 (carbonyl C); 153.17 (azole C); 135.64, 135.15, 128.98, 126.19, 126.14, 126.89 (aromatic ring carbons), 63.14 (C-H); 16.7 (CH$_3$); the CF$_3$ carbon appears as a quartet centred at about 123.2 ppm.

EXAMPLE 17

This Example illustrates the preparation of 1-(trifluoromethylphenyl)-1-(trifluoromethoxyphenyl)-2-(2H-tetrazol-2-yl)propan-1-ol.

The Grignard reagent from 4-bromotrifluoromethoxybenzene (2.41 g) was prepared in a similar manner to that described in Example 3 from magnesium turnings (0.24) in dry tetrahydrofuran (14 ml) with iodine (1 crystal) as an activator. To the Grignard solution was added dropwise over 10 minutes 2-(2H-tetrazol-2-yl)p-trifluoromethylpropiophenone from Example 16 (2.7 g in dry tetrahydrofuran (10 ml), then the reaction stirred for 1 hour. The reaction was worked up as for previous examples, by pouring into water, acidifying with aqueous hydrochloric acid and extracting the product into diethyl ether, which was dried over anhydrous sodium sulphate and evaporated. The residual oil (4.3 g) was purified by h.p.l.c. on silica gel eluting with 5:1 hexane/ethyl acetate to give a colourless oil 2.3 g.

$^1$H NMR CDCl$_3$ δ ppm: 1.53 (3H, d); ca. 4.9 (1H, broad); 6.2 (1H, q); 7.0–7.8 (8H, m); 8.4 (1H, s).

EXAMPLE 18

This Example illustrates the preparation of 1-(4-trifluoromethyl-phenyl)-1-(4-trifluoromethoxyphenyl)-1-fluoro-2-(2H-tetrazol-2-yl)propane (Compound XXX).

This compound was prepared from the product of Example 17 by methods analogous to those described in Example 14.

Melting point 77°–78° C.

$^1$H NMR CDCl$_3$ δ ppm: ca. 1.76* (total 3H, 2 overlapping doublets); ca. 6.1 (1H, dq); 7.0–7.8 (8H, m); 8.33, 8.35* (total 1H, 2 singlets).

*These signals show the presence of 2 diastereoisomers in about 55/45 ratio.

EXAMPLE 19

This Example illustrates the preparation of 1,1-bis(3-fluoro-4-trifluoromethoxyphenyl)-2-(1,2,3,4-2H-tetrazol-2-yl)propan-1-ol.

Step A

2-Fluorophenol (56.03 g) was dissolved in carbon disulphide (100 ml). A solution of bromine (87.89 g) in carbon disulphide (30 ml) was added dropwise over a period of 5 hours with vigorous stirring. The mixture was allowed to stand overnight at room temperature, then was poured into water (80 ml). A saturated solution of sodium thiosulphate (200 ml) was added and the mixture shaken. The organic layer was separated, washed with saturated sodium bicarbonate solution (100 ml) and water (150 ml). The organic layer was dried over anhydrous sodium sulphate, then was evaporated to leave 2-fluoro-4-bromophenol as an orange oil. This was distilled at about 14 mm Hg pressure. The fractions distilling at 89°–92° C. (65 g 98% pure by g.l.c.) and 92°–96° C. (10 g 97% pure by g.l.c.) were collected.

$^1$H NMR δ 5.25 (1H, broad signal); 6.9 (1H, triplet); 7.16 (1H, m); 7.24 (1H, m).

Step B

2-Fluoro-4-bromophenol (55 g) from step (a) was dissolved in carbon tetrachloride (154 g) and charged to an autoclave vessel made of Hastelloy. The vessel was evacuated and cooled in liquid nitrogen. Anhydrous hydrogen fluoride (205 g) was then transferred to the vessel. The temperature was raised to 135° C. and the pressure to 720 p.s.i. over about 3 hours. The reaction mixture was maintained at 135° C. for a further 5 hours 40 minutes and then was allowed to cool to room temperature over 9 hours. The vessel was cooled in ice and carefully vented. The contents were poured into ice, the organic materials were extracted into dichloromethane which was shaken with aqueous sodium carbonate solution, then dried over anhydrous magnesium sulphate. The solution was filtered and volatiles evaporated on a steam bath. The mixture was then distilled at water pump vacuum (ca. 20 mmHg) and the fraction distilling at 50°–54° C. (17 g) collected (92% pure by g.l.c.). This was shown to be 2-fluoro-4-bromotrifluoromethoxybenzene by g.c.m.s.

$^1$H NMR CDCl$_3$δppm: 7.1–7.5 (aromatic protons). Coupling constants $J_{H5-H6}$ 9.4; $J_{H3-H5}$ 2.3; $J_{F-H3}$ 9.4; $J_{F-H5}$ 1.3; $J_{FH6}$ 8.8; $J_{CF3-f}$ 1; all values in HZ
also isolated was a fraction distilling at 78°–80° C. (10.5 g) which was 85% at 2-fluoro-4-bromodifluorochloromethoxybenzene.

Step C

Magnesium turnings (1.22 g) and iodine (1 crystal) were added to dry tetrahydrofuran (10 ml) under a nitrogen atmosphere. A solution of 3-fluoro-4-trifluoromethoxybromobenzene (12.95 g) in dry tetrahydrofuran (30 ml) was placed in a dropping funnel. About 10% of this was added to the mixture, and the Grignard reaction began immediately. The rest of the mixture was added dropwise with stirring, and the temperature rose until the solvent was at reflux. After the addition was complete the mixture was allowed to cool, then a solution of methyl-2-(2H-tetrazol-2-yl)propionate (3.9 g) in dry tetrahydrofuran (10 ml) was added with stirring. An exotherm was noted, and the reaction was allowed to stir at room temperature for 30 minutes. The mixture was then poured into water (100 ml). The mixture was acidified by adding 3M hydrochloric acid (100 ml) and then extracted with diethyl ether (3×100 ml). The combined ethereal extracts were dried over anhydrous sodium sulphate and evaporated to a brown oil (10 g). This was chromatographed on silica gel eluting with 4:1 hexane/ethylacetate to give an oil (1.85 g).

$^1$H NMR CDCl$_3$δppm: 1.57 (3H, d); 4.96 (1H, s); 6.10 (1H, q); 7.1–7.6 (6H, m); 8.42 (1H, s).

EXAMPLE 20

This Example illustrates the preparation of 1,1-bis(3-fluoro-4-trifluoromethoxyphenyl)-1-fluoro-2-(2H-tetrazol-2-yl)propane (Compound XXIX).

The tertiary alcohol from Example 19 (0.9 g) was dissolved in dry dichloromethane (20 ml). Diethylaminosulphurtrifluoride (DAST 0.34 ml ex Aldrich) was dissolved in dry dichloromethane (30 ml) and then cooled to −70° C. under an atmosphere of nitrogen. The tertiary alcohol solution was added dropwise over 1 hour, and after a further 1 hour at −70° C., the mixture was allowed to warm to room temperature and stand for 18 hours. The mixture was then poured into water (50 ml) and the organic layer was separated, washed with more water (2×50 ml) then was dried over anhydrous sodium sulphate. The solvents were evaporated to give a brown oil (1 g) which was purified by h.p.l.c. on a silica gel column eluting with 5:1 n-hexane/ethylacetate, to produce an oil (0.66 g).

$^1$H NMR CDCl$_3$δppm: 1.75 (3H, d); ca. 6.0 (1H, dq); 7.0–7.5 (6H, m); 8.36 (3H, s).

EXAMPLE 21

This Example illustrates the preparation of 1,1-bis(4-trifluoromethoxyphenyl)-1-chloro-2-(2H-tetrazol-2-yl propane (Compound XVIII).

To a solution of imidazole (1.23 g) and 1,1-bis(4-trifluoromethoxyphenyl)-1-hydroxy-2-(2H-tetrazol-2-yl)propane prepared as described in Example b 3 (1.34 g) in dry acetonitrile (50 ml) under an atmosphere of nitrogen, was added thionylchloride (1.07 g). A precipitate appeared and the reaction was stirred at room temperature for 5 hours. The mixture was then poured into water (100 ml) and extracted with ether (2×70 ml). The organic extracts were combined and washed well with saturated aqueous sodium bicarbonate solution (50 ml) then with water (50 ml). The organic layer was dried over anhydrous magnesium sulphate, and evaporated to give a yellow oil which was purified by h.p.l.c. on a silica gel column eluted with n-hexane/ethyl acetate (5:1) to give a colourless oil (900 mg).

$^1$H NMR CDCl$_3$δppm: 1.98 (3H, d); 6.20 (1H, q); 7.0–7.6 (8H, m); 8.35 (1H, s)

$^{19}$F NMR CDCl$_3$δ relative to CFCl$_3$ −58.31 and −58.36 ppm. (2×OCF$_3$)

EXAMPLE 22

In a manner analogous to that described in Example 21, the following compounds were prepared.

(i) 1-(4-chlorophenyl)-1-(4-trifluoromethylphenyl)-1-chloro-2-(2H-tetrazol-2-yl)propane (Compound XXVI).

$^1$H NMR CDCl$_3$δppm: 1.96 (3H, d); 6.23 (1H, q); 7.1–7.7 (8H, m); 8.36 (1H, s).

(ii) 1,1-bis(4-trifluoromethylphenyl)-1-chloro-2-(2H-tetrazol-2-yl propane (Compound XVII). (a colourless oil).

$^1$H NMR CDCl$_3$δppm: 1.98 (3H, d); 6.30 (1H, q); 7.3–7.7 (8H, m); 8.37 (1H, s).

EXAMPLE 23

This Example illustrates the preparation of 1,1-bis(4-trifluoromethoxyphenyl)-2-(2H-tetrazol-2-yl)propane (Compound XVI).

The 1,1-bis(4-trifluoromethoxyphenyl)-1-chloro-2-(2H-tetrazol-2-yl)propane prepared as described above in Example 21 (0.7 g) was mixed with dry toluene (15 ml), tri n-butyltinhydride (0.44 g) and α,α'-Azoisobutyronitrile (AIBN) (3 crystals). The reaction was heated at 65° C. for 3½ hours. G.l.c. analysis showed the presence of some starting material, so a further portion of tributyltin hydride (0.08 ml) was added and heating continued for a further 3 hours at 65° C. The mixture was evaporated on a rotary evaporator, and the residue passed through a silica column eluted with 5:1 n-hexane/ethylacetate to remove the bulk of the tin residues. The oil obtained by evaporation of the solvent was purified further by h.p.l.c. eluting with the same solvent to give a clear oil (520 mg.).

$^1$H NMR CDCl$_3$δppm: 1.6 (3H, d); ca. 4.7 (1H, d); ca. 5.8 (1H, dq); 6.9–7.5 (8H, m); 8.35 (1H, s).

EXAMPLE 24

This Example illustrates the preparation of 1,1-bis-(4-trifluoromethylphenyl)-2-(2H-tetrazol-2-yl)propane (Compound IX).

This compound was prepared by reduction of the chloro compound from Example 22ii by procedures analogous to those described in Example 23.

Melting point 94°–96° C.

$^1$H NMR CDCl$_3$δppm: 1.62 (3H, d); 4.80 (1H, d J 13 Hz); ca. 5.9 (1H, dq J 7 and 13 HZ); 7.2–7.8 (8H, m); 8.35 (1H, s).

EXAMPLE 25

This Example illustrates the preparation of 1,1-bis(4-trifluoromethylphenyl)-1-fluoro-2-(1,2,3,4-1H-tetrazol-1-yl)propane (Compound XXXVIII).

This compound was prepared by treatment of the 1,1-bis(4-trifluoromethylphenyl)-2-(1,2,3,4-1H-tetrazol-1-yl) propan-1-ol from Example 5 with diethylaminosulphurtrifluoride, by a similar procedure as outlined in Example 14. The compound was obtained as a glass.

$^1$H NMR CDCl$_3$δ: 1.67 (3H, d); 6.04 (1H, dq); 7.48, 7.70 (each 4H, s); 8.74 (1H, d-split long range coupling to the F).

$^{19}$F NMR CDCl$_3$δ: (relative to CFCl$_3$) −63.43, −63.54 (each 3F, s); −168.4, −168.73 (total 1F).

EXAMPLE 26

This Example illustrates the preparation of methyl 2-(1,2,3,-triazolyl)propionates.

1,2,3-Triazole (16.65 g) was mixed with methyl 2-bromopropionate (40.26 g) and anhydrous potassium carbonate (66.61 g) in acetone (500 ml). The mixture was heated under reflux for 3 hours, then allowed to stand for 18 hours. The mixture was filtered and the filtrate evaporated on a rotary evaporator to give an oil. This oil was distilled using a vacuum pump at about 1 mm Hg. The fraction distilling between 68° and 78° C. was >97% the [2-H]-isomer (A) (10 g). A fraction distilling between 78° and 95° C. was collected, being 93%A (3 g). The pot residue when no more distilled was essentially pure [1-H]-isomer (B) by g.l.c. (18.8 g).

Isomer A

Methyl 2-(2H-1,2,3-triazol-2-yl)propionate $^1$H NMR CDCl$_3$δppm: 1.92 (3H, d); 3.75 (3H, s); 5.45 (1H, q); 7.68 (2H, s).

Isomer B

Methyl 2-(1H-1,2,3-triazol-1-yl)propionate $^1$H NMR CDCl$_3$δppm: 1.85 (3H, d); 3.78 (3H, s); 5.54 (1H, q); 7.75, 7.76 (2H, 2 singlets very close together)

EXAMPLE 27

Using methods analogous to those described in Example 3, the following compounds were prepared from the intermediates obtained in Example 26.

(i) 1,1-bis(4-trifluoromethoxyphenyl)-2-(1H-1,2,3-triazol-1-yl)propan-1-ol.

Pale yellow solid melting point 135°–137° C.

$^1$H NMR CDCl$_3$δppm: 1.54 (3H, d); 5.8 (1H, q); 5.84 (1H, s); 6.96–7.65 (8H as 4 2H doublets); 7.52 and 7.83 (each 1H, s).

(ii) 1,1-bis-(4-trifluoromethoxyphenyl)-1-hydroxy-2-(2H-triazol-2-yl)propan-1-ol.

(Prepared as a clear pale orange oil).

$^1$H NMR CDCl$_3$δppm: 1.45 (3H, d); 5.65 (1H, s); 5.80 (1H, q); 7.0–7.6 (8H as 4×2H doublets); 7.47 (2H, s).

EXAMPLE 28

The following compounds were prepared from the alcohols obtained in Example 27 using methods analogous to those described in Example 14.

(i) 1,1-bis(4-trifluoromethoxyphenyl)-1-fluoro-2-(1H-1,2,3-triazol-1-yl)propane (Compound XXXVI).

Melting point 105°–109° C.

Prepared as a white solid.

$^1$H NMR CDCl$_3$δppm: 1.54 (3H, d); ca. 5.9 (1H, dq); 7.0–7.6 (9H, m, 8 aromatic plus 1 triazole H); 7.7 (1H, d—small long range coupling to F).

(ii) 1,1-bis(4-trifluoromethoxyphenyl)-1-fluoro-2-(2H-1,2,3-triazol-2-yl)propane (Compound XXXVII)

Solid-melting point 108°–110° C.

$^1$H NMR CDCl$_3$δppm: 1.69 (3H, d); ca. 5.8 (1H, dq); 6.9–7.7 (10H, 8 aromatic plus 2 triazole H).

EXAMPLE 29

This Example illustrates the preparation of 1,1-bis(4-trifluoromethylphenyl)-1-chloro-2-(1,2,4-1H-triazol-1-yl)propane (Compound V).

Thionyl chloride (0.43 g) was added dropwise to a stirred mixture of 1,1-bis(4-trifluoromethylphenyl)-2-(1,2,4-1H-triazol-1-yl)propan-1-ol (0.5 g), imidazole (0.49 g) and acetonitrile (30 cm$^3$) and the mixture kept for 2 hours after which excess toluene was added and the mixture subjected to azeotropic distillation to remove unreacted thionyl chloride. The residue was partitioned between ethyl acetate and dilute aqueous sodium bicarbonate solution. The organic phase was separated, washed with water, dried over anhydrous magnesium sulphate and concentrated by evaporation of the solvent. The residual oil was purified by hplc using a silica gel column eluted with a mixture of dichloromethane (3 parts by volume) and ethyl acetate (1 part by volume) to yield two products. The faster running (minor) product (30 mg) was identified as 1,1-bis(4-trifluoromethylphenyl)-2-(1,2,4-1H-triazol-1-yl)prop-1-ene, and the slower running (major) product (120 mg) was identified as 1,1-bis(4-trifluoromethylphenyl)-1-chloro-2-(1,2,4-1H-triazol-1-yl)propane.

NMR (CDCl$_3$)δ: 1.82 (d, 3H); 5.73 (q, 1H); 7.3–7.67 (m, 8H); 7.72 (s, 1H); 8.23 (s, 1H).

EXAMPLE 30

In a manner analogous to that described in Example 29, the following compounds were prepared.

(i) 1,1-bis(4-chlorophenyl)-1-chloro-2-(1H-1,2,4-triazol-1-yl)propane (Compound IV)

Prepared as a glass.

$^1$H NMR CDCl$_3$δppm: 1.79 (3H, d); 5.61 (1H, q); 7.0–7.5 (8H, m); 7.75 and 8.17 (each 1H, s).

(ii) 1,1-bis(4-trifluoromethoxyphenyl)-1-chloro-2-(1H-1,2,4-triazol-1-yl)propane (Compound XXXIV).

Prepared as an oil which crystallised on standing.

$^1$H NMR CDCl$_3$δppm: 1.80 (3H, d); 5.65 (1H, q); 7.0–7.6 (8H, m); 7.72 and 8.2 (each 1H, s).

EXAMPLE 31

This Example illustrates the preparation of 1,1-bis(4-chlorophenyl)-2-(1H-1,2,4-triazol-1-yl)propane (Compound XXXIII).

Method A 1,1-bis(4-chlorophenyl)-1-chloro-2-(1H-1,2,4-triazol-1-yl)propane (0.6 g) from Example 34 (i) was dissolved in dry toluene (15 ml) and stirred under an atmosphere of nitrogen. To this was added tri-n-butyltinhydride, and the mixture heated at 100° C. for 12 hours. The mixture was then evaporated on a rotary evaporator to give a colourless oil (1.8 g). This material was purified by repeated chromatography on silica gel eluting with 4:1 ethyl acetate/n-hexane to give the product (200 mg) as an oil.

$^1$H NMR CDCl$_3$δppm: 1.54 (3H, d); 4.42 (1H, d); ca. 5.0 (1H, m); 6.95–7.4 (8H, m); 7.71 and 7.88 (each 1H, s).

Method B

Stage 1

1,1-bis(4-chlorophenyl)-2-(1H-1,2,4-triazol-1-yl)propan-1-ol (2.0 g) from Example 3xi was dissolved in dry toluene (40 ml), and a catalytic amount of p-toluene sulphonic acid added. The mixture was refluxed in a round bottom flask fitted with a soxhlet extractor filled with molecular sieves (4A) and condenser. Reflux was continued until there was no starting material remaining on tlc. The mixture was poured into water and extracted, washed with water (3X) then dried over anhydrous magnesium sulphate and evaporated on a rotary evaporator. The product was purified by chromatography on silica gel eluted with CH$_2$Cl$_2$/ethylacetate (3:2). 1,1-bis(4-chlorophenyl)-2-(1H-1,2,4-triazol-1-yl)prop-1-ene was obtained as a white solid (1.0 g) by recrystallisation from hexane.

$^1$H NMR CDCl$_3$ δ ppm: 2.3 (3H, s); 6.7–7.5 (8H, m); 7.65 and 8.0 (each 1H, s).

Method B

Stage 2

The olefin from stage 1 (1 g) was dissolved in ethanol (200 ml) and hydrogenated in an autoclave at 110 atmospheres and 70° C. for 20 hours. The catalyst was filtered off and the ethanol evaporated on a rotary evaporator to leave a yellow oil. The product was purified by chromatography on silica gel eluting with CH$_2$Cl$_2$/ethyl acetate (3:2). The product was obtained as an oil (100 mg), with an nmr identical to that obtained by method A.

EXAMPLE 32

This Example illustrates the preparation of 1,1-bis(4-trifluoromethoxyphenyl)-2-(1H-1,2,4-triazol-1-yl)propane (Compound XXXV).

1,1-bis(4-trifluoromethoxyphenyl)-1-chloro-2-(1H-1,2,4-triazol-1-yl)propane from Example 30(ii) was reacted with tri-n-butyltin hydride using procedures analogous to those described in Example 23 to give the desired product as a gum.

$^1$H NMR CDCl$_3$ δ ppm: 1.55 (3H, d); 4.5 (1H, d); ca. 5.0 (1H, overlapping dq); 6.9–7.5 (8H, m); 7.72 and 7.86 (each 1H, s).

EXAMPLE 33

Using a process analogous to that described in Example 32, the following compound was prepared.

1,1-bis(4-trifluoromethylphenyl)-2-(1H-1,2,4-triazol-1-yl)propane (Compound VIII).

$^1$H NMR CDCl$_3$ δ ppm: 1.55 (3H, d); ca. 4.65 (1H, d); ca. 5.16 (1H, dq); 7.1–7.7 (8H, m); 7.76, 7.86 (each 1H, s).

EXAMPLE 34

This Example illustrates the preparation of 1,1-bis(4-trifluoromethoxyphenyl)-1-fluoro-2-(1H-pyrazol-1-yl)propane (Compound XII).

1,1-bis(4-trifluoromethoxyphenyl)-2-(1H-pyrazol-1-yl)propan-1-ol, prepared as described in UK Patent Application No. 2156807A, was reacted with DAST using procedures analogous to those described in Example 14 to yield the desired product as an oil.

$^1$H NMR CDCl$_3$ δ (ppm): 1.54 (3H, d); ca. 5.5 (1H, dq); 6.1 (1H, t); 6.9–7.6 (10H, m, 8 aromatic and 2 pyrazole H).

EXAMPLE 35

This Example illustrates the preparation of 1,1-bis(4-trifluoromethylphenyl)-1-fluoro-2-(1H-pyrazol-1-yl)propane (Compound XIII).

1,1-bis(4-trifluoromethylphenyl)-2-(1H-pyrazol-1-yl)propan-1-ol, prepared as described in UK Patent Application No. 2156807A, was fluorinated using procedures described in Example 14 to produce the desired product as a white solid melting point 64°–66° C.

$^1$H NMR CDCl$_3$ δ ppm: 1.54 (3H, d); ca. 5.56 (1H, dq); 6.15 (1H, t); 7.2–7.7 (10H, m, 8 aromatic plus 2 pyrazole protons).

EXAMPLE 36

This Example illustrates the preparation of 1,1-bis(4-trifluoromethylphenyl)-1-chloro-2-(1H-pyrazol-1-yl)propane (Compound XXXI).

1,1-bis(4-trifluoromethylphenyl)-2-(1H-pyrazol-1-yl)propan-1-ol was reacted with thionyl chloride under conditions described in Example 29 to produce a mixture of the desired product and some 1,1-bis(4-trifluoromethylphenyl)-2-(1H-pyrazol-1-yl)prop-1-ene by elimination. This olefin impurity was removed by h.p.l.c. on silica gel eluting with 5:1 hexane/ethyl acetate and obtained as a solid m.pt 104°–106° C. The desired material was obtained as an oil 94% pure by glc.

$^1$H NMR CDCl$_3$ δppm: 1.77 (3H, d); 5.7 (1H, q); 6.18 (1H, t); 7.2–7.7 (10H, m, 8 aromatic and 2 pyrazole H).

EXAMPLE 37

This Example illustrates the preparation of 1,1-bis(4-trifluoromethylphenyl)-2-(1H-pyrazol-1-yl)propane (Compound XXXII).

The halide from Example 36 was reduced as described in Example 23 to give a gum which solidified, melting point 78°–80° C.

$^1$H NMR CDCl$_3$ δ ppm: 1.53 (3H, d); 4.66 (1H, d); 5.06 (1H, m); 6.02 (1H, t); 7.1–7.7 (10H, m, 8 aromatic plus 2 pyrazole H).

Biological Data

The insecticidal activity of Compounds of the invention is set out in the following Table II as a grading of A, B or C where A indicates that 80–100% mortality was observed, B indicates that 50–79% mortality was observed and C indicates that 0–49% mortality was observed. The tests were conducted by supporting the test species on a medium (eg. leaves of a suitable food plant, or filter paper) and spraying the pests and medium (contact test—"+" in the Table) or by spraying the medium before placing the pests thereon (residual test—"*" in the Table). Assessment of mortality was made 72 hours after spraying except for houseflies (*Musca domestica*) where the assessment was made after 24 hours. In the test the compounds were used in the form of aqueous composition comprising 500 parts per million of the compound prepared by dissolving the compound in mixture of solvents consisting of 4 parts by volume by acetone and 1 part by volume of diacetone alcohol and diluting the solution with water containing 0.01% by weight of a wetting agent. ("Lissapol" NX—"Lissapol" is a Registered Trade Mark).

TABLE I

| Compound No. | Cp* (larvae) | Hv* (larvae) | Db* (larvae) | Md+ (adults) | Bg* (adults) |
|---|---|---|---|---|---|
| II | A | C | A | C | C |
| III | A | A | A | A | B |
| IV | A | C | A | B | C |
| V | A | C | A | C | B |
| VI | A | B | B | A | C |
| VII | A | A | A | A | A |
| VIII | A | A | A | A | B |
| IX | A | A | A | A | A |
| X | A | A | A | B | C |
| XI | A | A | A | A | A |
| XII | C | B | C | C | C |
| XIII | C | C | A | A | B |
| XVI | A | A | A | A | A |
| XVII | A | A | A | A | A |
| XVIII | A | A | A | A | A |
| XIX | C | C | A | C | C |
| XX | A | B | A | A | B |
| XXI | C | A | C | C | C |
| XXII | A | C | C | A | A |
| XXIII | C | C | A | A | B |
| XXIV | A | A | A | A | A |
| XXV | A | A | A | A | A |
| XXVI | B | A | — | C | A |
| XXVII | A | A | A | A | A |
| XXVIII | A | C | A | A | C |
| XXIX | A | A | A | A | A |
| XXX | A | A | A | A | A |
| XXXI | C | C | C | C | C |
| XXXII | C | C | C | C | C |
| XXXIII | A | C | B | C | C |
| XXXIV | A | A | A | A | A |
| XXXV | A | A | B | C | C |
| XXXVI | A | A | A | C | C |
| XXXVII | B | A | A | C | C |
| XXXX | C | C | C | C | C |
| XXXXI | A | A | A | A | A |
| XXXXII | C | C | C | C | B |
| XXXXIII | B | C | C | C | A |
| XXXXV | C | A | A | C | C |
| XXXXVI | A | A | A | A | A |
| XXXXVII | A | A | A | A | A |

Test Species

Cp=*Chilo partellus* (maize stem borers)
Hv=*Heliothis virescens* (tobacco budworms)
Db=*Diabrotica balteata* (rootworms)
Md=*Musca domestica* (houseflies)
Bg=*Blattella gramanica* (cockroaches)

In Table II it can be seen that the compounds exhibit useful insecticidal and acaricidal activity against a number of test species representing a wide variety of insect pests of economic importance.

I claim:

1. A compound of formula (I):

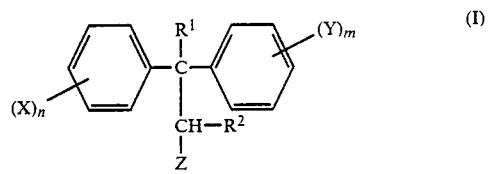

wherein $R^1$ is hydrogen or halogen, $R^2$ is methyl or ethyl, X and Y are independently selected from halogen, haloalkyl, haloalkoxy, alkyl and alkoxy, m and n are each zero, one or two, and Z is a pyrazolyl, triazolyl or tetrazolyl group.

2. A compound according to claim 1 wherein the group Z is 1H-pyrazol-1-yl, 1,2,4-1H-triazol-1-yl, 1,2,3-1H-triazol-1-yl, 1,2,3-2H-triazol-2-yl or 1,2,3,4-2H-tetrazol-2-yl or 1,2,3,4-1H-tetrazol-1-yl.

3. A compound according to claim 2 wherein $R^1$ is hydrogen, fluorine or chlorine.

4. A compound according to claim 3 where $R^2$ is methyl.

5. A compound according to claim 1 selected from:
1,1-bis-(4-chlorophenyl)-1-fluoro-2-(1H-pyrazol-1-yl)propane;
1,1-bis-(4-chlorophenyl)-1-fluoro-2-(1,2,4-1H-triazol-1-yl)propane;
1,1-bis(4-chlorophenyl)-1-fluoro-2-(1,2,3,4-2H-tetrazol-2-yl)propane;
1,1-bis(4-chlorophenyl)-1-chloro-2-(1,2,4-1H-triazol-1-yl)-propane;
1,1-bis(4-trifluoromethylphenyl)-1-chloro-2-(1,2,4-1H-triazol-1-yl)propane;
1,1-bis(4-trifluoromethylphenyl)-1-fluoro-2-(1,2,4-1H-triazol-1-yl)propane;
1,1-bis(4-trifluoromethylphenyl)-1-fluoro-2-(1,2,3,4-2H-tetrazol-2-yl)propane;
1,1-bis(4-trifluoromethylphenyl)-2-(1,2,4-1H-triazol-1-yl)-propane;
1,1-bis(4-trifluoromethylphenyl)-2-(1,2,3,4-2H-tetrazol-2-yl)propane;
1,1-bis(4-trifluoromethoxyphenyl)-1-fluoro-2-(1,2,4-1H-triazol-1-yl)propane;
1,1-bis(4-trifluoromethoxyphenyl)-1-fluoro-2-(1,2,3,4-2H-tetrazol-2-yl)propane;
1,1-bis(4-trifluoromethoxyphenyl)-1-fluoro-2-(1H-pyrazol-1-yl) propane;
1,1-bis(4-trifluoromethylphenyl)-1-fluoro-2-(1H-pyrazol-1-yl)propane;
1,1-bis(4-difluoromethoxyphenyl)-1-fluoro-2-(1,2,4-1H-triazol-1-yl)propane;
1,1-bis(4-difluoromethoxyphenyl)-1-fluoro-2-(1,2,3,4-2H-tetrazol-2-yl) propane;
1,1-bis(4-trifluoromethoxyphenyl)-2-(1,2,3,4-2H-tetrazol-2-yl)propane;
1,1-bis(4-trifluoromethylphenyl)-1-chloro-2-(1,2,3,4-2H-tetrazol-2-yl)propane;
1,1-bis(4-trifluoromethoxyphenyl)-1-chloro-2-(1,2,3,4-2H-tetrazol-2-yl)propane;
1,1-bis(4-methylphenyl)-1-fluoro-2-(1,2,3,4-2H-tetrazol-2-yl)propane;
1,1-bis(4-fluorophenyl)-1-fluoro-2-(1,2,3,4-2H-tetrazol-2-yl)propane;
1,1-bis(4-prop-2-ylphenyl)-1-fluoro-2-(1,2,3,4-2H-tetrazol-2-yl)propane;
1,1-bis(4-bromophenyl)-1-fluoro-2-(1,2,3,4-2H-tetrazol-2-yl)propane;

1,1-bis(3-trifluoromethyl-4-chlorophenyl)-1-fluoro(1,2,3,4-2H-tetrazol-2-yl)propane;

1,1-bis(3,4-difluorophenyl)-1-fluoro-2-(1,2,3,4-2H-tetrazol-2-yl)propane;

1-(4-chlorophenyl)-1-(4-trifluoromethylphenyl)-1-fluoro-2-(1,2,3,4-2H-tetrazol-2-yl)propane;

1-(4-chlorophenyl)-1-(4-trifluoromethylphenyl)-1-chloro-2-(1,2,3,4-2H-tetrazol-2-yl)propane;

1-(4-chlorophenyl)-1-(4-trifluoromethoxyphenyl)-1-fluoro-2-(1,2,3,4-2H-tetrazol-2-yl)propane;

1-(4-ethoxyphenyl)-1-(4-trifluoromethoxyphenyl)-1-fluoro-2-(1,2,3,4-2H-tetrazol-2-yl)propane;

1,1-bis(3-fluoro-4-trifluoromethoxyphenyl)-1-fluoro-2-(1,2,3,4-2H-tetrazol-2-yl)propane;

1-(4-trifluoromethoxyphenyl)-1-(trifluoromethylphenyl)-1-fluoro-2-(1,2,3,4-2H-tetrazol-2-yl)propane;

1,1-bis(4-trifluoromethylphenyl)-1-chloro-2-(1H-pyrazol-1-yl)propane;

1,1-bis(4-trifluoromethylphenyl)-2-(1H-pyrazol-1-yl)propane;

1,1-bis(4-chlorophenyl)-2-(1,2,4-1H-triazole-1-yl)propane;

1,1-bis(4-trifluoromethoxyphenyl)-1-chloro-2-(1,2,4-1H-triazol-1-yl)propane;

1,1-bis(4-trifluoromethoxyphenyl)-2-(1,2,4-1H-triazol-1-yl)propane;

1,1-bis(4-trifluoromethoxyphenyl)-1-fluoro-2-(1,2,3-1H-triazol-1-yl)propane;

1,1-bis(4-trifluoromethoxyphenyl)-1-fluoro-2-(1,2,3-2H-triazol-2-yl)propane;

1,1-bis(4-trifluoromethylphenyl)-2-(1,2,3,4-1H-tetrazol-1-yl)propane.

6. A compound of formula (IIA)

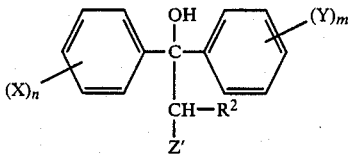
(IIA)

wherein $R^2$, X, Y, m and n are as defined in claim 1 and Z' is Z as defined in claim 1 provided that when Z' is 1,2,3,4-2H-tetrazole, $R^2$ is ethyl or n and m are other than 1 and that when Z' is an azolyl group containing 3 nitrogen atoms other than 1,2,3-1H-triazol-1-yl or 1,2,3,-2H-triazol-2-yl, $R^2$ is ethyl.

7. An insecticidal composition comprising a compound selected from the group consisting of compounds of formula (I):

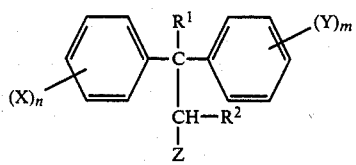
(I)

and compounds of formula (IIA):

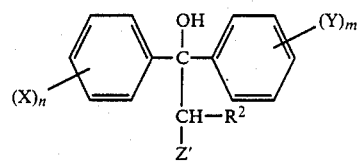
(IIA)

wherein $R^1$ is hydrogen or halogen, $R^2$ is methyl or ethyl, X and Y are independently selected from halogen, haloalkyl, haloalkoxy, alkyl and alkoxy, m and n are each zero, one or two, Z is a pyrazolyol, triazolyl or tetrazolyl group, and Z' is the same as Z provided that when Z' is 1,2,3,4-2H-tetrazole, $R^2$ is ethyl or n and m are other than 1, and when Z' is an azolyl group containing 3 nitrogen atoms other than 1,2,3-1H-triazol-1-yl or 1,2,3-2H-triazol-2-yl, $R^2$ is ethyl, in combination with a carrier or diluent.

8. A method of controlling or eliminating invertebrate pests, which method comprises administering to the pest or to the environment thereof a pesticidally effective amount of a compound selected from the group consisting of compounds of formula (I):

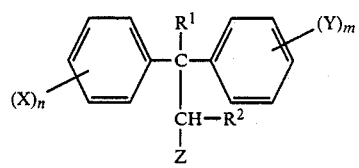
(I)

or formula (IIA)

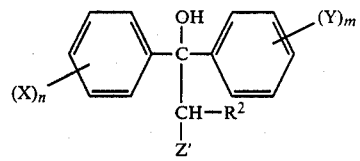
(IIA)

wherein $R^1$ is hydrogen or halogen, $R^2$ is methyl or ethyl, X and Y are independently selected from halogen, haloalkyl, haloalkoxy, alkyl and alkoxy, m and n are each zero, one or two, Z is a pyrazolyl, triazolyl or tetrazolyl group, and Z' is the same as Z provided that when Z' is 1,2,3,4-2H-tetrazole, $R^2$ is ethyl or n and m are other than 1, and when Z' is an azolyl group containing 3 nitrogen atoms other than 1,2,3-1H-triazol-1-yl or 1,2,3-2H-triazol-2-yl, $R^2$ is ethyl, in combination with a carrier or diluent.

9. A compound according to claim 1, wherein Z is triazolyl.

10. A compound acording to claim 1, wherein Z is tetrazolyl.

11. A compound according to claim 9, wherein the triazole is 1,1-bis(4-trifluoromethylphenyl)-2-(1,2,4-1H-triazol-1-yl)-propane.

12. A compound according to claim 10, wherein the tetrazole is 1,1-bis(4-difluoromethoxyphenyl)-1-fluoro-2-(1,2,3,4-2H-tetrazol-2-yl)propane.

13. The compound 1-(4-trifluoromethylphenyl)-1-(4-trifluoromethoxyphenyl)-2-(1,2,3,4-2H-tetrazol-2-yl)-propan-1-ol.

* * * * *